United States Patent
Jana

(10) Patent No.: US 9,266,100 B2
(45) Date of Patent: Feb. 23, 2016

(54) PRE-CARBURIZED MOLYBDENUM-MODIFIED ZEOLITE CATALYST AND USE THEREOF FOR THE AROMATIZATION OF LOWER ALKANES

(75) Inventor: Suman Kumar Jana, Gujarat (IN)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 561 days.

(21) Appl. No.: 13/697,640

(22) PCT Filed: May 17, 2011

(86) PCT No.: PCT/EP2011/002435
§ 371 (c)(1),
(2), (4) Date: Nov. 13, 2012

(87) PCT Pub. No.: WO2011/144319
PCT Pub. Date: Nov. 24, 2011

(65) Prior Publication Data
US 2013/0066126 A1 Mar. 14, 2013

(30) Foreign Application Priority Data
May 20, 2010 (EP) ................... 10005263

(51) Int. Cl.
| | | |
|---|---|---|
| B01J 29/06 | (2006.01) | |
| B01J 29/48 | (2006.01) | |
| B01J 29/064 | (2006.01) | |
| B01J 29/46 | (2006.01) | |
| B01J 29/068 | (2006.01) | |
| B01J 29/44 | (2006.01) | |
| B01J 29/072 | (2006.01) | |
| B01J 29/42 | (2006.01) | |
| B01J 29/076 | (2006.01) | |
| C07C 2/76 | (2006.01) | |
| B01J 37/08 | (2006.01) | |

(52) U.S. Cl.
CPC .............. *B01J 29/48* (2013.01); *B01J 29/061* (2013.01); *B01J 29/064* (2013.01); *B01J 29/068* (2013.01); *B01J 29/072* (2013.01); *B01J 29/076* (2013.01); *B01J 29/42* (2013.01); *B01J 29/44* (2013.01); *B01J 29/46* (2013.01); *C07C 2/76* (2013.01); *B01J 37/08* (2013.01); *B01J 2229/16* (2013.01); *B01J 2229/40* (2013.01); *B01J 2229/42* (2013.01); *C07C 2523/28* (2013.01); *C07C 2529/064* (2013.01); *C07C 2529/068* (2013.01); *C07C 2529/072* (2013.01); *C07C 2529/076* (2013.01); *C07C 2529/40* (2013.01); *C07C 2529/42* (2013.01); *C07C 2529/46* (2013.01); *C07C 2529/48* (2013.01)

(58) Field of Classification Search
USPC .................................... 502/60, 64, 66, 74, 77
See application file for complete search history.

(56) References Cited

U.S. PATENT DOCUMENTS

| | | | |
|---|---|---|---|
| 2007/0249740 A1* | 10/2007 | Iaccino et al. ................ | 518/726 |
| 2008/0249342 A1* | 10/2008 | Iaccino et al. ................ | 585/402 |
| 2008/0312483 A1 | 12/2008 | Ichikawa et al. | |
| 2010/0029999 A1* | 2/2010 | Uphade et al. ................ | 585/407 |

FOREIGN PATENT DOCUMENTS

| | | |
|---|---|---|
| EP | 2140939 A1 | 1/2010 |
| WO | 0123087 A1 | 4/2001 |
| WO | 0210099 A2 | 2/2002 |
| WO | 2007127026 A2 | 11/2007 |
| WO | 2009097067 A2 | 8/2009 |

OTHER PUBLICATIONS

Beyer, Hermann K.; "Dealumination Techniques for Zeolites"; Post-Synthesis Modification I; Molecular Sieves; vol. 3; 2002; pp. 203-255.
Extended European Search Report; European Application No. 10005263.8; Date of Mailing: Sep. 17, 2010; 7 Pages.
Ismagilov et al.; "Direct Conversion of Methane on Mo/ZSM-5 Catalysts to Produce Benzene and Hydrogen: Achievements and Perspectives"; Energy and Environmental Science; vol. 1; 2008; pp. 526-541.
International Search Report; International Application No. PCT/EP2011/002435; International Filing Date: May 17, 2011; Date of Mailing: Aug. 22, 2011; 5 Pages.
Written Opinion of the International Searching Authority; International Application No. PCT/EP2011/002435; International Filing Date: May 17, 2011; Date of Mailing: Aug. 22, 2011; 7 Pages.
Shu et al.; "A Highly Selective and Coking-Resistant Catalysts for Methane Dehydrocondensation"; Chemistry Letters; Mar. 2002; pp. 418-419.
Wang et al.; "Dehydrogenation and Aromatization of Methane Under Non-Oxidizing Conditions"; Catalysis Letters; vol. 21; 1993; pp. 35-41.

* cited by examiner

Primary Examiner — Elizabeth Wood
(74) Attorney, Agent, or Firm — Cantor Colburn LLP

(57) ABSTRACT

The present invention relates to a method for producing a zeolite catalyst useful for aromatization of a lower alkane, a zeolite catalyst useful for aromatization of a lower alkane obtainable by said method and a process for aromatization of a lower alkane using the zeolite catalyst of the present invention.

14 Claims, No Drawings

PRE-CARBURIZED MOLYBDENUM-MODIFIED ZEOLITE CATALYST AND USE THEREOF FOR THE AROMATIZATION OF LOWER ALKANES

CROSS-REFERENCE TO RELATED APPLICATIONS

This application is a 371 of International Application No. PCT/EP2011/002435, filed May 17, 2011, which claims priority to European Application No. 10005263.8, which is currently pending and published as EP 2571616, filed May 20, 2010, both of which are hereby incorporated by reference in its entirety.

TECHNICAL FIELD

The present invention relates to a method for producing a molybdenum-modified zeolite catalyst useful for aromatization of a lower alkane, a zeolite catalyst useful for aromatization of a lower alkane obtainable by said method and a process for aromatization of a lower alkane using the zeolite catalyst of the present invention.

BACKGROUND ART

It has been previously described that lower alkanes can be directly converted into higher hydrocarbons using a molybdenum-modified medium pore-size zeolite catalyst.

Wang (1993) Catal Lett 21, 35-41, for instance, describes the catalytic conversion of methane into benzene under non-oxidizing conditions using a ZSM-5 zeolite catalyst on which molybdenum has been deposited.

A major drawback of the use of molybdenum-modified medium pore-size zeolite catalyst for the aromatization of lower alkanes is that coke is deposited on the catalyst surface which quickly reduces catalyst activity.

Shu (2002) Chemistry Letters, 418-419 describes that de-alumination by acid reflux of Mo-loaded zeolites like ZSM-5 and MCM-22 leads to decreased coke formation in methane aromatization reactions. Shu teaches that this reduction in coke formation is caused by a reduction of the number of Brønsted acid sites on the catalyst surface.

WO 02/10099 describes that the catalyst activity in a methane aromatization process can be stabilized by activating the molybdenum-loaded ZSM-5 catalyst with a combined stream which comprises over 25 mole-% of hydrogen and methane prior to contacting the catalyst with the methane feed.

DISCLOSURE OF INVENTION

It was an object of the present invention to provide a further improved process for converting lower alkanes into aromatics. This is achieved by providing the subject matter as described herein below and as characterized in the claims.

Accordingly, the present invention provides a method for producing a zeolite catalyst useful for aromatization of a lower alkane comprising:

(a) providing a zeolite catalyst precursor comprising 2-10 wt % molybdenum (Mo) and 0-2 wt % of one or more additional elements selected from Groups 6-11 of the Periodic Table; and (b) contacting the provided zeolite catalyst precursor with a pre-carburizing gas stream comprising a lower alkane and 50-90 mole-% of an inert diluent gas at a temperature that is gradually increased from 20-250° C. to the temperature useful for aromatization and keeping the temperature constant for 0-60 minutes at the temperature useful for aromatization.

In the context of the present invention, it was found that the pre-carburization of Mo-loaded H-ZSM-5 zeolite catalyst precursor with a combined stream of the lower alkane methane and inert diluent gas like nitrogen at a constantly increasing temperature e.g. from 100° C. to the temperature useful for aromatization (750° C.) remarkably improves the stability/performance of the catalyst for methane aromatization. Moreover, it was found that catalyst performance is even further improved in case the catalyst precursor is pre-carburized under the combined stream of methane and nitrogen at a constantly increasing temperature to the temperature useful for aromatization and is subsequently kept for e.g. 15 minutes at the temperature useful for aromatization.

Accordingly, the zeolite catalyst produced by the method of the present invention is useful in a process for converting a feedstream comprising a lower alkane to a product stream comprising aromatic hydrocarbons. This process for converting a lower alkane to aromatic hydrocarbons is also described herein as "lower alkane aromatization". Preferably, the "lower alkane" is methane ($CH_4$), ethane ($C_2H_6$) or a mixture thereof. Preferably, said mixture comprises up to 20 mole-% ethane in methane. Most preferably, the "lower alkane" is methane ($CH_4$). The aromatic hydrocarbons produced by the present lower alkane aromatization process include benzene, toluene and xylenes (commonly denoted as "BTX").

The term "pre-carburizing gas stream" as used herein relates to a gas stream comprising a lower alkane and 50-90 mole-% of an inert diluent gas. The term "inert diluent gas" as used herein relates to an element or compound (or a mixture thereof) which is gaseous at the conditions used for pre-carburization and which does not participate in and/or adversely interfere with the chemical reactions that occur when the catalyst is contacted with the pre-carburizing gas stream during pre-carburization. Preferably, the inert diluent gas is selected from the group consisting of nitrogen ($N_2$), helium (He) and argon (Ar). Hydrogen ($H_2$), for instance, is not an "inert diluent gas" since it is known to act as a reducing agent when comprised in the pre-carburizing gas stream. Accordingly, the "inert diluent gas" of the present invention does not comprise $H_2$ or other reducing components. The maximum allowable amount of other components like reducing components in the pre-carburizing gas stream is 10 mole-%, preferably up to 5 mole-% and more preferably up to 2 mole-%. Most preferably, the pre-carburizing gas stream consists essentially of lower alkane and inert diluent gas (i.e. less than 1 mole-% of other components).

In the method of the present invention, the temperature is gradually increased from room temperature (i.e. about 20° C.)-250° C. to the temperature useful for aromatization. Preferably, the temperature is gradually increased from 100-250° C. to the temperature useful for aromatization. The temperature useful for aromatization can be easily determined by the person skilled in the art; see e.g. Ismagilov (2008) Energy and Environmental Science 526-541. Preferably, the temperature useful for aromatization is 600-850° C., more preferably 700-750° C. The pressure at which the aromatization reaction of the present invention can be carried out can be easily determined by the skilled person and preferably is 0.2-5 atmosphere, more preferably 0.5-2 atm.

The term "gradually increased temperature" or "temperature that is gradually increased" as used herein means that the temperature is increased at a predetermined rate over a period of time. In the method according to the invention, the temperature is preferably increased at a rate of about 20° C./min or less, more preferably at a rate of about 10° C./min or less and most preferably at a rate of about 5° C./min.

When the temperature useful for aromatization is reached after gradually increasing said temperature starting from 20-250° C., the temperature may be kept constant for a certain period of time before, for instance, switching the gaseous feed of the catalyst from the pre-carburization stream to a feed-stream for aromatization. Preferably, the temperature is kept constant for 5-60 minutes at the temperature useful for aromatization after attaining said temperature useful for aromatization. Most preferably the temperature is kept constant for 15 minutes at the temperature useful for aromatization after attaining said temperature useful for aromatization. It is preferred to start aromatization reaction immediately after the pre-carburization. However, it is possible to cool down the catalyst after pre-carburization and then to later directly use the catalyst without having to redo the pre-carburization. In such cases time and carrier gas may be wasted and, hence, the efficiency of the process will decrease.

The term "zeolite catalyst precursor" or "catalyst precursor" as used herein relates to the zeolite-based composition at any stage prior to the pre-carburizing step (b) as described herein above.

Prior to the pre-carburization step, the zeolite catalyst precursor of the present invention comprises 2-10 wt % Mo, preferably 3-5 wt % Mo. In addition thereto, the zeolite catalyst precursor may further contain up to 2 wt %, preferably up to 0.5 wt % of one or more additional elements selected from Group 6-11 of the Periodic Table (IUPAC version of 22 Jun. 2007). In one embodiment, said one or more additional elements that may be comprised in the catalyst precursor are selected from Group 6-10 of the Periodic Table. Preferred additional elements are selected from the group consisting of tungsten (W), platinum (Pt), ruthenium (Ru), rhenium (Re), cobalt (Co), copper (Cu) and iron (Fe). Methods useful for determining the quantity of Mo and other elements comprised in the compositions as described herein are well known in the art and include AAS (Atomic Absorption Spectrometer) or ICP (Inductively Coupled Plasma Spectrometry) analysis.

Microporous aluminosilicate zeolites useful in a process for lower alkane aromatization are well known in the art. Preferably the zeolite is a medium-pore size zeolite having a pore size of about 5-6 Å. Suitable medium-pore size zeolites are 10-ring zeolites. i.e. the pore is formed by a ring consisting of 10 $SiO_4$ tetrahedra. In one preferred embodiment, the zeolite is of the pentasil type. Most preferably, the zeolite is H-ZSM-5. Other zeolites known to be useful for lower alkane aromatization include, but are not limited to MCM-22 and H-ZSM-11.

It is preferred that the zeolite is in the hydrogen form: i.e. having at least a portion of the original cations associated therewith replaced by hydrogen. Methods to convert an aluminosilicate zeolite to the hydrogen form are well known in the art. A first method involves direct ion exchange employing an acid. A second method involves base exchange followed by calcination.

The zeolite of the present invention may be dealuminated. Accordingly, the zeolite preferably has a Si/Al ratio of 10-50. Means and methods to obtain dealuminated zeolite are well known in the art and include, but are not limited to the acid leaching technique; see e.g. Post-synthesis Modification I; Molecular Sieves, Volume 3; Eds. H. G. Karge, J. Weitkamp; Year (2002); Pages 204-255. In the context of the present invention it was found that using a dealuminated H-ZSM-5 zeolite having a Si/Al ratio of 10-50 improves the performance/stability of the catalyst. Means and methods for quantifying the Si/Al ratio of a dealuminated zeolite are well known in the art and include, but are not limited to AAS (Atomic Absorption Spectrometer) or ICP (Inductively Coupled Plasma Spectrometry) analysis.

The zeolite catalyst precursor that is subjected to the pre-carburization method of the present invention may be produced by any conventional method. Preferably, the provided zeolite catalyst is produced by a method comprising depositing Mo and optionally one or more additional elements selected from Group 6-11 of the Periodic Table on the zeolite using an incipient wetness method which comprises the steps of contacting a zeolite with a solution comprising a soluble Mo-salt and optionally a solution comprising one or more additional elements selected from Group 6-11 of the Periodic Table; and drying the zeolite to provide a zeolite catalyst precursor. Deposition of metal(s) onto the zeolite can also be carried out by using impregnation technique in aqueous solution under acidic as well as basic conditions. In one embodiment, said one or more additional elements that may be deposited are selected from Group 6-10 of the Periodic Table.

The Mo and one or more additional elements may be deposited on the zeolite concurrently by contacting the zeolite with a solution comprising both a soluble Mo-salt and (a) soluble salt(s) comprising one or more additional elements selected from Group 6-11 of the Periodic Table. Alternatively, the Mo and one or more additional elements may be deposited on the zeolite subsequently by contacting the zeolite with a solution comprising Mo and a different solution comprising one or more additional elements selected from Group 6-11 of the Periodic Table. When one or more additional elements are deposited, it is preferred that Mo is deposited first. The solution used for depositing the Mo and said optional additional element(s) preferably is an aqueous solution. In one embodiment of the present invention, the zeolite catalyst precursor is dried in air.

After drying, the catalyst precursor on which Mo and the optional additional element(s) are deposited is calcined in air, preferably in moisture free air. Preferably, the catalyst precursor is calcined at 500-650° C. and a pressure of 1 atm for 1-5 hrs. Most preferably the catalyst precursor is calcined at 600° C. for 2 hrs.

Accordingly, a method for producing a zeolite catalyst useful for aromatization of a lower alkane is provided comprising:

(a) contacting a zeolite with a solution comprising molybdenum (Mo) and optionally a solution comprising one or more additional elements selected from Group 6-11 of the Periodic Table;

(b) drying and calcining the product of step (a) to provide a zeolite catalyst precursor comprising 2-10 wt % molybdenum (Mo) and 0-2 wt % of one or more additional elements selected from Group 6-11 of the Periodic Table; and (c) contacting the provided zeolite catalyst precursor with a pre-carburizing gas stream comprising a lower alkane and 50-90 mole-% of an inert diluent gas at a temperature that is gradually increased from 20-250° C. to the temperature useful for aromatization and keeping the temperature constant for 0-60 minutes at the temperature useful for aromatization.

Preferably, the zeolite catalyst prepared by the method of the present invention and which is useful in a process for the aromatization of a lower alkane further comprises a binder. Preferably, the binder is selected from the group consisting of lanthanum-exchanged Kaolin and alpha alumina and most preferably the binder is La-exchanged kaolin binder. In the context of the present invention it was found that the use of binder improves the catalyst performance.

Accordingly, the dried and calcined zeolite catalyst precursor composition may subsequently be bound with a binder before subjecting said catalyst precursor to pre-carburization. Therefore, the catalyst and the binder are thoroughly mixed, preferably at a weight ratio of 4-1:1, most preferably at a weight ratio of about 2:1. The catalyst mixture may then be formed into pellets, for instance by pressing the mixed catalyst and binder composition at e.g. 10 tons of pressure. The pressed catalyst composition may subsequently be crushed and sieved to provide zeolite catalyst precursor in particulate form. The crushed solids containing particle sizes from 0.5 to 1.0 mm are preferably selected for catalytic use.

In a further embodiment, a zeolite catalyst useful for aromatization of a lower alkane is provided that is obtainable by the method for producing a zeolite catalyst of the present invention.

In yet another embodiment of the invention, a process for aromatization of a lower alkane is provided comprising contacting the catalyst of the present invention with a feedstream comprising a lower alkane at conditions useful for aromatization. Accordingly, the present invention provides a process for the aromatization of a lower alkane comprising: producing a zeolite catalyst useful for aromatization of a lower alkane according to the method of the present invention; and contacting said catalyst with a feedstream comprising a lower alkane at conditions useful for aromatization. Preferably, the aromatization process of the present invention is performed at non-oxidizing conditions.

As used herein, the term "feedstream" relates to the gaseous stream which is brought into contact with the catalyst to convert the therein comprised lower alkane into aromatic hydrocarbons. In one embodiment, the feedstream is different from the pre-carburizing gas stream in that it e.g. does not comprise an inert diluent. Preferably, the feedstream consists of lower alkane, more preferably 0-20 mole-% ethane in methane and most preferably, the feedstream consists of pure methane.

The conditions useful for aromatization can be easily determined by the person skilled in the art; see e.g. Ismagilov (2008) Energy and Environmental Science 526-541. Again, the temperature useful for aromatization may be 600-850° C. and preferably 700-750° C. Furthermore, the aromatization reaction as described herein preferably is performed at a WHSV 0.1-2 h$^{-1}$ and/or a pressure 0.2-5 atm.

MODE(S) FOR CARRYING OUT THE INVENTION

The present invention will now be more fully described by the following non-limiting Examples.

Comparative Example 1

Non-Pre-Carburized 3.5% Mo H-ZSM-5

In order to prepare Mo/H-ZSM-5 zeolite, 0.65 g ammonium molybdate tetrahydrate was dissolved in 15 ml demineralised water. 10 g of powder H-ZSM-5 having Si/Al ratio of 11.5 was added to the above solution. The resulting paste was thoroughly mixed and dried at 100° C. for 12 h. The dried catalyst mass was further heated up to 600° C. at a rate of 5° C./min followed by calcined at 600° C. for 2 h in the presence of moisture-free air.

To prepare the binder, 0.19 g lanthanum nitrate hexahydrate was dissolved in 120 ml demineralised water. Subsequently, 6 g of powder kaolin was added to the above solution. The mixture was heated at 95-98° C. for 24 h under continuous stirring. Resulting La-exchanged kaolin was separated by filtration. The retained solid mass was washed with 2 liters of demineralised water and dried at 100° C. for 12 h. Dried La-exchanged kaolin was calcined in a muffle furnace at 650° C. for 4 h under flowing moisture-free air (flow: 100 ml/min). The solid mass was then cooled to room temperature. La content in the binder material was determined by AAS (Atomic Absorption Spectrometer) to be 1 wt. % La on Kaolin.

The catalyst compositions comprising of Mo-containing H-ZSM-5 based zeolites and La-exchanged kaolin binder were prepared in particle form by mixing thoroughly the catalyst and the binder in the ratio of 2:1. The catalyst mixture was then pressed at 10 ton pressure to make pellets. The pressed catalyst compositions were crushed and sieved. The crushed solids containing particle sizes from 0.5 to 1.0 mm were selected for catalytic use.

2.0 g catalyst particles were loaded in a down flow fixed bed micro-catalytic reactor. The temperature of the reactor is heated under constant $N_2$ flow. After attaining the temperature of the reactor to the desired reaction temperature (750° C.), $N_2$ flow is stopped and a pure methane flow is fed to the catalyst bed (20 ml/min at 1 atm) and the reaction started. The Weight Hourly Space Velocity (WHSV) was 0.4 h$^{-1}$. Unconverted methane and the products formed were analysed by an on-line Gas Chromatograph equipped with Petrocol DH 50.2 column, using a Flame Ionization Detector. The obtained results are summarized in Table 1.

TABLE 1

| Time/h | Methane Conv./% | Product distribution—Selectivity (wt %) | | | |
|---|---|---|---|---|---|
| | | C2-C5 | Benzene | BTX | C9+ aromatics |
| 1 | 14.5 | 11.4 | 64.8 | 67.5 | 21.1 |
| 2 | 13.5 | 13.0 | 71.6 | 74.7 | 12.3 |
| 3 | 12.7 | 14.2 | 73.8 | 77.2 | 8.6 |
| 4 | 11.4 | 16.4 | 74.6 | 78.1 | 5.5 |
| 5 | 10.2 | 18.4 | 75.7 | 79.0 | 2.6 |
| 6 | 8.6 | 21.0 | 75.7 | 78.5 | 0.5 |
| 7 | 7.5 | 24.0 | 73.4 | 75.7 | 0.3 |
| 8 | 6.8 | 27.4 | 70.3 | 72.4 | 0.2 |
| 9 | 6.1 | 30.1 | 67.7 | 69.7 | 0.2 |

Comparative Example 2

Non-Pre-Carburized 3.5% Mo/Dealuminated H-ZSM-5

The experimental procedures for comparative Example 2 were identical to Comparative Example 1 with the exception that dealuminated H-ZSM-5 zeolite was used.

The Mo-modified dealuminated H-ZSM-5 zeolite of Comparative Example 2 was prepared as follows. 0.65 g ammonium molybdate tetrahydrate was dissolved in 15 ml demineralised water. 10 g of powder dealuminated H-ZSM-5 having Si/Al ratio of 12.6 was added to the above solution. The resulting paste was thoroughly mixed and dried at 100° C. for 12 h. The dried catalyst mass was further heated up to 600° C. at a rate of 5° C./min followed by calcined at 600° C. for 2 h in the presence of moisture-free air.

10 g parent H-ZSM-5 having Si/Al ratio of 11.5 was dispersed in 200 ml of aqueous 6 (N) nitric acid solution in a round bottom flask. The mixture was heated at 95-100° C. under stirring for 5 h. The solid mass was filtered out and washed thoroughly with 2 liters of demineralised water and dried at 100° C. for 12 h. The Si/Al ratio of the zeolite was determined by AAS (Atomic Absorption Spectrometer) to be 12.6.

The same process conditions as in Comparative Example 1 were used. Unconverted methane and the products formed were analysed by an on-line Gas Chromatograph equipped with Petrocol DH 50.2 column, using a Flame Ionization Detector. The obtained results are summarized in Table 2.

TABLE 2

| Time/h | Methane Conv./% | Product distribution—Selectivity (wt %) | | | |
|---|---|---|---|---|---|
| | | C2-C5 | Benzene | BTX | C9+ aromatics |
| 1 | 15.7 | 11.0 | 55.3 | 57.7 | 31.3 |
| 2 | 14.7 | 12.6 | 65.0 | 67.9 | 19.5 |
| 3 | 13.2 | 14.4 | 70.7 | 74.0 | 11.6 |
| 4 | 12.1 | 15.9 | 72.7 | 76.1 | 8.0 |
| 5 | 10.9 | 18.3 | 74.0 | 77.4 | 4.3 |
| 6 | 9.9 | 20.4 | 74.3 | 77.6 | 2.0 |
| 7 | 8.9 | 22.8 | 73.2 | 76.2 | 1.0 |
| 8 | 8.1 | 26.0 | 70.7 | 73.4 | 0.6 |
| 9 | 7.4 | 28.2 | 69.1 | 71.5 | 0.3 |

Comparative Example 3

3.5% Mo/Daluminated H-ZSM-5 Pre-Carburized with Pure Methane at Constantly Increasing Temperature from 100-700° C. and Holding Time of 0.25 h at 700° C.

The 3.5% Mo/dealuminated H-ZSM-5 of Comparative Example 3 was prepared as described under Comparative Example 2.

In comparative Example 3, however, the catalyst was first subjected to pre-carburization using a pre-carburization gas stream consisting of pure methane and thus which does not comprise an inert diluent.

Therefore 2.0 g catalyst particles were loaded in a down flow fixed bed micro-catalytic reactor and pre-carburized in the following way:

Step 1: Exposed to the flowing moisture-free $N_2$ (flow: 25 ml/min) at 100° C. for 0.25 h.

Step 2: Exposed to the moisture-free stream consisting of pure methane (20 ml/min) under a constantly increasing temperature ramp of 5° C./min from 100° C. to 700° C., followed by holding at that temperature for 0.25 h at 700° C.

Step 3: Exposed to a moisture-free $N_2$ (flow: 50 ml/min) at 700° C., followed by increasing the temperature from the pre-carburization temperature to 750° C. using the ramp 5° C./min.

After pre-carburization of catalyst and attaining the temperature of the reactor to the desired reaction temperature (750° C.), $N_2$ flow is stopped and the methane flow fed to the catalyst bed is set at 20 ml/min at 1 atm and the reaction started. The Weight Hourly Space Velocity (WHSV) was 0.4 $h^{-1}$. Unconverted methane and the products formed were analysed by an on-line Gas Chromatograph equipped with Petrocol DH 50.2 column, using a Flame Ionization Detector. The obtained results are summarized in Table 3.

TABLE 3

| Time/h | Methane Conv./% | Product distribution—Selectivity (wt %) | | | |
|---|---|---|---|---|---|
| | | C2-C5 | Benzene | BTX | C9+ aromatics |
| 1 | 14.2 | 12.4 | 63.6 | 66.2 | 21.4 |
| 2 | 13.6 | 14.0 | 69.8 | 72.6 | 13.4 |
| 3 | 13.0 | 14.4 | 70.9 | 74.0 | 11.6 |
| 4 | 12.2 | 15.7 | 71.4 | 74.8 | 9.5 |
| 5 | 11.3 | 16.9 | 71.1 | 74.6 | 8.5 |
| 6 | 10.4 | 19.1 | 71.2 | 74.5 | 6.4 |
| 7 | 9.6 | 22.1 | 69.4 | 72.4 | 5.5 |
| 8 | 8.8 | 25.3 | 68.9 | 71.8 | 2.9 |
| 9 | 8.1 | 28.4 | 68.0 | 70.6 | 1.0 |

Comparative Example 4

3.5% Mo/Dealuminated H-ZSM-5 Pre-Carburized with Methane and $H_2$ at Constantly Increasing Temperature from 100-700° C. and Holding Time of 0.25 h at 700° C.

Comparative Example 4 is identical to Comparative Example 3, with the exception that the pre-carburizing gas stream consists of methane (10 ml/min) and $H_2$ (10 ml/min). Accordingly, the pre-carburizing gas stream does not comprise an inert diluent.

The same process conditions as in Comparative Example 3 were used. Unconverted methane and the products formed were analysed by an on-line Gas Chromatograph equipped with Petrocol DH 50.2 column, using a Flame Ionization Detector. The obtained results are summarized in Table 4.

TABLE 4

| Time/h | Methane Conv./% | Product distribution—Selectivity (wt %) | | | |
|---|---|---|---|---|---|
| | | C2-C5 | Benzene | BTX | C9+ aromatics |
| 1 | 13.9 | 11.0 | 59.2 | 62.7 | 26.3 |
| 2 | 13.7 | 11.7 | 62.8 | 65.6 | 22.7 |
| 3 | 13.2 | 12.5 | 66.8 | 70.0 | 17.5 |
| 4 | 12.4 | 13.7 | 69.4 | 72.8 | 13.5 |
| 5 | 11.6 | 15.5 | 71.2 | 74.6 | 9.9 |
| 6 | 10.3 | 17.6 | 71.9 | 75.1 | 7.3 |
| 7 | 9.6 | 19.9 | 72.3 | 75.3 | 4.8 |
| 8 | 8.8 | 21.6 | 72.0 | 74.9 | 3.5 |
| 9 | 7.7 | 22.8 | 71.4 | 74.4 | 2.8 |

Comparative Example 5

3.5% Mo/Dealuminated H-ZSM-5 Pre-Carburized at 750° C. for 15 Min with Methane and $N_2$ The 3.5% Mo/dealuminated H-ZSM-5 of Comparative Example 5 was prepared as described under Comparative Example 2.

In Example 5, however, the catalyst was subjected to pre-carburization using a pre-carburization gas stream containing methane and $N_2$. Therefore, 2.0 g catalyst particles were loaded in a down flow fixed bed micro-catalytic reactor and pre-carburized in the following way:

Step 1: Exposed to the flowing moisture-free $N_2$ (flow: 25 ml/min) at 100° C. for 0.25 h, followed by increase temperature to 750° C. under a constantly increasing temperature range of 5° C./min.

Step 2: Exposed to the moisture-free stream containing methane (10 ml/min) and $N_2$ (30 ml/min) at 750° C. for 0.25 h. Hence, the temperature was not gradually increased during pre-carburization.

Step 3: Exposed to a moisture-free $N_2$ (flow: 50 ml/min) at 750° C. for 0.1 h.

After pre-carburization of catalyst and attaining the temperature of the reactor to the desired reaction temperature (750° C.), $N_2$ flow is stopped and the methane flow fed to the catalyst bed is set at 20 ml/min at 1 atm and the reaction started. Pure methane was used as a feedstream for the reaction. The Weight Hourly Space Velocity (WHSV) was $0.4\ h^{-1}$. Unconverted methane and the products formed were analysed by an on-line Gas Chromatograph equipped with Petrocol DH 50.2 column, using a Flame Ionization Detector. The obtained results are summarized in Table 5.

TABLE 5

| Time/h | Methane Conv./% | Product distribution—Selectivity (wt %) | | | |
|---|---|---|---|---|---|
| | | C2-C5 | Benzene | BTX | C9+ aromatics |
| 1 | 14.6 | 12.5 | 67.9 | 70.6 | 16.9 |
| 2 | 13.8 | 12.7 | 71.8 | 74.8 | 12.5 |
| 3 | 13.4 | 13.9 | 71.1 | 74.4 | 11.7 |
| 4 | 12.3 | 15.2 | 71.7 | 75.2 | 9.6 |
| 5 | 11.6 | 16.8 | 70.6 | 74.3 | 8.9 |
| 6 | 10.4 | 18.8 | 71.2 | 75.3 | 5.9 |
| 7 | 9.8 | 20.2 | 71.5 | 75.5 | 4.3 |
| 8 | 9.4 | 22.4 | 70.1 | 74.1 | 3.5 |
| 9 | 8.7 | 23.9 | 69.8 | 73.8 | 2.3 |

Example 1

3.5% Mo/Dealuminated H-ZSM-5 Pre-Carburized with Methane and $N_2$ at Constantly Increasing Temperature from 100-750° C. with No Holding Time at 750° C.

Example 1 is identical to Comparative Example 5 with the exception that the catalyst was pre-carburized in the following way:

Step 1: Exposed to the flowing moisture-free $N_2$ (flow: 25 ml/min) at 100° C. for 0.25 h.

Step 2: Exposed to the moisture-free stream containing methane (10 ml/min) and $N_2$ (30 ml/min) under a constantly increasing temperature ramp of 5° C./min from 100° C. to 750° C. Hence, the temperature was gradually increased during pre-carburization.

Step 3: Exposed to a moisture-free $N_2$ (flow: 50 ml/min) at 750° C. for 0.1 h.

Subsequently, the catalyst is switched to the methane feedstream. The same process conditions as in the comparative Example 1 were used. Unconverted methane and the products formed were analysed by an on-line Gas Chromatograph equipped with Petrocol DH 50.2 column, using a Flame Ionization Detector. The obtained results are summarized in Table 6.

TABLE 6

| Time/h | Methane Conv./% | Product distribution—Selectivity (wt %) | | | |
|---|---|---|---|---|---|
| | | C2-C5 | Benzene | BTX | C9+ aromatics |
| 1 | 15.0 | 11.6 | 65.1 | 67.9 | 20.5 |
| 2 | 14.4 | 12.4 | 70.7 | 73.7 | 13.9 |
| 3 | 13.3 | 13.6 | 75 | 78.2 | 8.2 |
| 4 | 12.3 | 15.4 | 76 | 79.2 | 5.4 |
| 5 | 11.4 | 17.0 | 75.8 | 78.9 | 4.1 |
| 6 | 10.6 | 17.5 | 76.7 | 79.8 | 2.7 |
| 7 | 9.8 | 19.1 | 75.4 | 78.7 | 2.2 |
| 8 | 9.5 | 21.1 | 73.9 | 77.1 | 1.8 |
| 9 | 8.8 | 23.0 | 72.4 | 75.6 | 1.4 |

Example 2

3.5% Mo/Dealuminated H-ZSM-5 Pre-Carburized with Methane and $N_2$ at Constantly Increasing Temperature from 100-750° C. with Holding Time of 0.25 h at 750° C.

Example 2 is identical to Example 1 with the exception that the catalyst was pre-carburized in the following way:

Step 1: Exposed to the flowing moisture-free $N_2$ (flow: 25 ml/min) at 100° C. for 0.25 h.

Step 2: Exposed to the moisture-free stream containing methane (10 ml/min) and $N_2$ (30 ml/min) under a constantly increasing temperature ramp of 5° C./min from 100° C. to 750° C. followed by holding at 750° C. for 0.25 h.

Step 3: Exposed to moisture-free $N_2$ (flow: 50 ml/min) at 750° C. for 0.1 h.

The same process conditions as in Example 1 were used. Unconverted methane and the products formed were analysed by an on-line Gas Chromatograph equipped with Petrocol DH 50.2 column, using a Flame Ionization Detector. The obtained results are summarized in Table 7.

TABLE 7

| Time/h | Methane Conv./% | Product distribution—Selectivity (wt %) | | | |
|---|---|---|---|---|---|
| | | C2-C5 | Benzene | BTX | C9+ aromatics |
| 1 | 15.0 | 11.9 | 67.8 | 70.9 | 17.2 |
| 2 | 14.5 | 12.4 | 71.4 | 74.7 | 12.9 |
| 3 | 13.6 | 14.2 | 72.3 | 75.7 | 10.1 |
| 4 | 13.1 | 15.3 | 72.9 | 76.3 | 8.4 |
| 5 | 12.4 | 16.8 | 73.3 | 76.8 | 6.4 |
| 6 | 11.6 | 18.1 | 73.1 | 76.7 | 5.2 |
| 7 | 10.9 | 19.2 | 72.7 | 76.4 | 4.4 |
| 8 | 10.4 | 20.7 | 71.9 | 75.6 | 3.7 |
| 9 | 10.1 | 21.9 | 71.5 | 75.2 | 2.9 |

Example 3

3.5% Mo/Dealuminated H-ZSM-5 Pre-Carburized with Methane and $N_2$ at Constantly Increasing Temperature from 200-750° C. with Holding Time of 0.25 h at 750° C.

Example 3 is identical to Example 1 with the exception that the catalyst was pre-carburized in the following way:

Step 1: Exposed to the flowing moisture-free $N_2$ (flow: 25 ml/min) at 200° C. for 0.25 h.

Step 2: Exposed to the moisture-free stream containing methane (10 ml/min) and $N_2$ (30 ml/min) under a constantly increasing temperature ramp of 5° C./min from 200° C. to 750° C. followed by holding at 750° C. for 0.25 h.

Step 3: Exposed to moisture-free $N_2$ (flow: 50 ml/min) at 750° C. for 0.1 h.

The same process conditions as in Example 1 were used. Unconverted methane and the products formed were analysed by an on-line Gas Chromatograph equipped with Petrocol DH 50.2 column, using a Flame Ionization Detector. The obtained results are summarized in Table 8.

TABLE 8

| Time/h | Methane Conv./% | Product distribution—Selectivity (wt %) | | | |
|---|---|---|---|---|---|
| | | C2-C5 | Benzene | BTX | C9+ aromatics |
| 1 | 14.1 | 11.2 | 67.8 | 71.0 | 17.8 |
| 2 | 13.8 | 12.3 | 71.3 | 74.3 | 13.4 |
| 3 | 12.8 | 13.8 | 74.1 | 77.2 | 9.0 |
| 4 | 12.4 | 14.4 | 72.3 | 75.5 | 10.1 |
| 5 | 11.5 | 15.6 | 73.3 | 76.6 | 7.8 |
| 6 | 10.7 | 17.6 | 72.5 | 75.9 | 6.5 |
| 7 | 10.2 | 18.2 | 72.1 | 75.7 | 6.1 |
| 8 | 9.8 | 19.7 | 70.8 | 74.6 | 5.7 |
| 9 | 9.5 | 21.5 | 69.3 | 73.2 | 5.3 |

Example 4

3.5$ Mo/Dealuminated H-ZSM-5 Pre-Carburized with Methane and $N_2$ at Constantly Increasing Temperature from 100-700° C. with Holding Time of 0.25 h at 700° C.

Example 4 is identical to Example 1 with the exception that the catalyst was pre-carburized in the following way:

Step 1: Exposed to the flowing moisture-free $N_2$ (flow: 25 ml/min) at 100° C. for 0.25 h.

Step 2: Exposed to the moisture-free stream containing methane (10 ml/min) and $N_2$ (30 ml/min) under a constantly increasing temperature ramp of 5° C./min from 100° C. to 700° C. followed by holding at 700° C. for 0.25 h.

Step 3: Exposed to moisture-free $N_2$ (flow: 50 ml/min) at 700° C., followed by increasing the temperature from 700° C. to 750° C. using the ramp 5° C./min.

The same process conditions as in Example 1 were used. Unconverted methane and the products formed were analysed by an on-line Gas Chromatograph equipped with Petrocol DH 50.2 column, using a Flame Ionization Detector. The obtained results are summarized in Table 9.

TABLE 9

| Time/h | Methane Conv./% | Product distribution—Selectivity (wt %) | | | |
|---|---|---|---|---|---|
| | | C2-C5 | Benzene | BTX | C9+ aromatics |
| 1 | 15.1 | 11.4 | 63.1 | 65.8 | 22.8 |
| 2 | 14.5 | 12.6 | 70.2 | 73.3 | 14.1 |
| 3 | 13.6 | 13.6 | 73.9 | 77.1 | 9.3 |
| 4 | 12.1 | 15.8 | 76.5 | 79.8 | 4.4 |
| 5 | 11.4 | 17.5 | 76.9 | 80.1 | 2.4 |
| 6 | 10.6 | 18.5 | 77.4 | 80.5 | 1.0 |
| 7 | 10.2 | 20.1 | 76.3 | 79.3 | 0.6 |
| 8 | 9.4 | 21.9 | 74.7 | 77.7 | 0.4 |
| 9 | 8.9 | 23.6 | 73.3 | 76.2 | 0.2 |

Comparative Example 5

3.5% Mo/Dealuminated H-ZSM-5 Pre-Carburized with Methane and $H_2$ at Constantly Increasing Temperature from 100-750° C. and Holding Time of 0.25 h at 750° C.

Comparative Example 5 is identical to Example 2, with the exception that the pre-carburizing gas stream consists of methane (10 ml/min) and $H_2$ (30 ml/min). Accordingly, the pre-carburizing gas stream does not comprise an inert diluent.

The same process conditions as in Example 2 were used. Unconverted methane and the products formed were analysed by an on-line Gas Chromatograph equipped with Petrocol DH 50.2 column, using a Flame Ionization Detector. The obtained results are summarized in Table 10.

TABLE 10

| Time/h | Methane Conv./% | Product distribution—Selectivity (wt %) | | | |
|---|---|---|---|---|---|
| | | C2-C5 | Benzene | BTX | C9+ aromatics |
| 1 | 14.1 | 15.6 | 63.1 | 65.4 | 19.0 |
| 2 | 13.9 | 16.1 | 68.0 | 70.1 | 13.8 |
| 3 | 13.5 | 16.3 | 71.9 | 73.1 | 10.6 |
| 4 | 12.9 | 16.7 | 72.3 | 74.0 | 9.3 |
| 5 | 12.4 | 17.5 | 73.7 | 74.9 | 7.6 |
| 6 | 11.5 | 18.1 | 73.8 | 75.8 | 6.1 |
| 7 | 10.5 | 18.8 | 74.6 | 76.5 | 4.7 |
| 8 | 9.6 | 19.8 | 74.0 | 76.4 | 3.8 |
| 9 | 8.8 | 21.3 | 73.7 | 76.0 | 2.7 |

By comparing the results in Tables 1-5 with Table 6 and by comparing the results in Table 10 with Table 7, it is clear that the pre-carburization of Mo-loaded H-ZSM-5 zeolite catalyst precursor with a combined stream of the lower alkane methane and inert diluent gas like nitrogen at a constantly increasing temperature from e.g. 100 to 750° C. remarkably improves the stability/performance of the catalyst for methane aromatization. Catalyst performance is even further improved in case the catalyst precursor is pre-carburized under the combined stream of methane and nitrogen at a constantly increasing temperature to the temperature useful for aromatization and is subsequently kept for e.g. 15 minutes at the temperature useful for aromatization; see Tables 6-7.

The invention claimed is:

1. A method for producing a zeolite catalyst useful for aromatization of a lower alkane comprising:
    contacting a medium pore zeolite catalyst precursor with a pre-carburizing gas stream comprising a pre-carburizing gas stream lower alkane and 50-90 mole-% of an inert diluent gas at a temperature that is increased from 20-250° C. at a rate of about 20° C./minute or less to a temperature useful for aromatization and keeping the temperature constant for 0-60 minutes at the temperature useful for aromatization to produce the zeolite catalyst;
    wherein the zeolite catalyst precursor comprises 2-10 wt % molybdenum (Mo) and 0-2 wt % of an additional element selected from Groups 6-11 of the Periodic Table.

2. The method of claim 1, wherein the zeolite precursor is produced by the process comprising:
    (i) contacting a zeolite with a solution comprising molybdenum (Mo) and optionally a solution comprising the additional element selected from Group 6-11 of the Periodic Table; and
    (ii) drying and calcining the zeolite to provide a zeolite catalyst precursor.

3. The method of claim 1, wherein the temperature is kept constant for 5-60 minutes at the temperature useful for aromatization after attaining said temperature useful for aromatization.

4. The method of claim 1, wherein the zeolite is dealuminated.

5. The method of claim 4, wherein the zeolite has a Si/Al ratio of 10-50.

6. The method of claim 1, wherein the zeolite catalyst precursor further comprises a binder.

7. The method of claim 6, wherein the binder is selected from the group consisting of La-exchanged Kaolin and alpha alumina.

8. The method of claim 1, wherein the temperature useful for aromatization is 600-850° C.

9. The method of claim 1, wherein the pre-carburizing gas stream consists of a pre-carburizing gas stream lower alkane and an inert diluent gas.

10. The method of claim 1, further comprising, subsequent to keeping the temperature constant for 0-60 minutes at the temperature useful for aromatization, contacting the zeolite catalyst with a feedstream lower alkane, wherein the lower alkane is methane ($CH_4$), ethane ($C_2H_6$) or a mixture thereof.

11. The method of claim 1, wherein the inert diluent gas is selected from the group consisting of nitrogen ($N_2$), helium (He) and argon (Ar).

12. The method of claim 1, wherein the zeolite is H-ZSM-5.

13. The method of claim 1, wherein the pre-carburizing gas stream lower alkane is methane and the inert diluent gas is nitrogen.

14. The method of claim 1, wherein the pre-carburizing gas stream consists essentially of methane and nitrogen.

\* \* \* \* \*